United States Patent [19]
Larice

[11] Patent Number: 5,738,661
[45] Date of Patent: Apr. 14, 1998

[54] MEDICAL DEVICE FOR HOLDING A FEEDING TUBE AND USE THEREOF

[76] Inventor: Gennaro Larice, 3 East Ave., Bayville, N.Y. 11709

[21] Appl. No.: 491,477

[22] Filed: Jun. 16, 1995

[51] Int. Cl.[6] ............................... A61M 5/32; A61F 5/44
[52] U.S. Cl. ........................ 604/180; 604/332; 604/277
[58] Field of Search ............................ 604/332–344, 604/277, 278, 180

[56] References Cited

U.S. PATENT DOCUMENTS

| | | | |
|---|---|---|---|
| 2,154,202 | 4/1939 | Gricks | 604/334 |
| 2,504,872 | 4/1950 | Perry . | |
| 3,021,843 | 2/1962 | Perry . | |
| 3,292,625 | 12/1966 | Marsan . | |
| 3,618,606 | 11/1971 | Brown et al. . | |
| 3,910,274 | 10/1975 | Nolan . | |
| 4,084,590 | 4/1978 | Caraway et al. . | |
| 4,519,793 | 5/1985 | Galindo | 604/180 |
| 4,530,525 | 7/1985 | Schneider . | |
| 4,553,967 | 11/1985 | Ferguson et al. . | |
| 4,583,977 | 4/1986 | Shishov et al. . | |
| 4,586,927 | 5/1986 | Jensen . | |
| 4,699,616 | 10/1987 | Nowak et al. . | |
| 4,701,163 | 10/1987 | Parks . | |
| 4,717,385 | 1/1988 | Cameron et al. . | |
| 4,869,719 | 9/1989 | Hogan . | |
| 4,925,216 | 5/1990 | Steer . | |
| 4,973,314 | 11/1990 | Garrett . | |
| 4,973,323 | 11/1990 | Kaczmarek et al. . | |
| 5,147,340 | 9/1992 | Lavender . | |
| 5,234,417 | 8/1993 | Parks et al. . | |
| 5,236,426 | 8/1993 | Schöttes et al. . | |
| 5,267,969 | 12/1993 | Hirsch et al. . | |
| 5,346,479 | 9/1994 | Schneider . | |
| 5,348,542 | 9/1994 | Ellis . | |
| 5,358,488 | 10/1994 | Suriyapa . | |
| 5,415,642 | 5/1995 | Shepherd | 604/344 |

*Primary Examiner*—Robert A. H. Clarke
*Attorney, Agent, or Firm*—Hoffmann & Baron

[57] ABSTRACT

A medical device for holding a feeding tube providing substantially rigid fastening of the tube to the patient. The device includes a drainage bag cooperatively disposed about the tube for containing any drainage that may occur through a body opening in which the tube is inserted. The drainage bag may be provided with a feeding tube-engaging port capable of accommodating feeding tubes of various diameters.

20 Claims, 5 Drawing Sheets

MEDICAL DEVICE FOR HOLDING A FEEDING TUBE AND USE THEREOF

BACKGROUND OF THE INVENTION

The present invention relates generally to medical devices for holding tubes or other types of catheters, and, more particularly, to medical devices for holding feeding tubes and having associated drainage bags.

Modern medical treatments may require the introduction of fluid into the body of a patient through an opening in the patient's skin tissue. Frequently, provision must also be made for collecting fluid which drains through the same opening.

For example, in gastrostomy, a feeding solution is introduced into the stomach of a patient by a tube passed through a stoma formed in the patient's abdominal wall. Gastric juices may be prone to leak out through the space between the outside of the tube and the stoma, necessitating packing with gauze or provision of complicated seals. In colostomy, artificial evacuation of the bowel through a stoma is aided by irrigation with a tube. The evacuated bowel contents must be captured. Furthermore, in the treatment of body wounds, frequent irrigation and drainage is required.

A number of devices currently available enable substantially rigid, permanent fixation of tubes for introduction of fluid into the body. Others provide drainage bags for collection of vented fluids.

Several devices exist which permit use of drainage bags in conjunction with tubes. Many of these are found in the field of colostomy. For example, U.S. Pat. No. 3,910,274 to Nolan discloses an irrigating cone fitted to the end of a tube for supplying irrigating fluid through a stoma. The stoma is surrounded by a drainage bag. The cone must be held in place manually by a patient. This type of device is not suited for long-term fixation of a feeding tube or the like.

In the area of wound treatment, U.S. Pat. No. 5,236,426 to Schöttes et al. discloses a drainage bag for surrounding a wound, with irrigation tubes passing through the bag. The tubes are fixed to the flexible bag, not to the patient. This can lead to severe discomfort for the patient when the tube shifts in the patient's body.

There is, therefore, a need in the prior art for a medical device for holding a tube that allows permanent, substantially rigid attachment of the tube to the patient and provides a drainage bag for substantially leak-free collection of liquid vented from a skin tissue opening through which the tube passes.

SUMMARY OF THE INVENTION

In its broadest aspect, the present invention is an apparatus for simultaneously introducing fluid into the body of a patient and providing drainage capability for an opening, such as a wound, in the patient. The apparatus of the present invention presupposes there is an opening in the skin tissue of a patient. Treatment of the patient generally includes introducing a fluid through the opening in the patient. Such treatment includes, for example, feeding a patient through the tube. Other treatments can include introducing medicaments, such as antibiotics, through the tube into the patient. Artisans will appreciate that yet further treatments may be contemplated using the present invention.

The present invention, which addresses the needs of the prior art, provides a medical device for holding a catheter, such as a feeding tube. The device includes a base plate for attachment to the skin tissue of the patient adjacent the opening in the skin tissue. The base plate has an aperture that permits the catheter to pass through it into the opening. The base plate also has a catheter retainer which provides substantially rigid fastening of the catheter to the base plate, and thus, to the patient's body. A drainage bag retainer on the base plate permits cooperative, sealing attachment of a drainage bag to the base plate. The drainage bag collects any drainage from the opening, and is also provided with a port through which the catheter can pass.

In one preferred embodiment, the opening may be a stoma provided for introduction of feeding fluid into the alimentary tract of a patient. Generally, a stoma will also result in fluid which drains from the opening in the patient, between the walls of the tube and the stoma. This fluid can be conveniently collected on a continuous basis while the feeding device remains in place.

As a result, the present invention provides a medical device for holding a catheter, such as a feeding tube, with a convenient arrangement of elements to simultaneously introduce fluid for treatment and collect fluid which may drain from the opening in the patient. The present invention also provides permanent, rigid attachment of the catheter to the patient, to prevent painful shifting of the catheter within the patient's body. The present invention further provides a method for simultaneous feeding and venting of bodily fluids through a stoma using a device in accordance with the invention.

For better understanding of the present invention, together with other and further objects and advantages, reference is made to the following description, taken in conjunction with the accompanying drawings, and its scope will be pointed out in the appended claims.

DETAILED DESCRIPTION OF THE INVENTION

Figure 1:
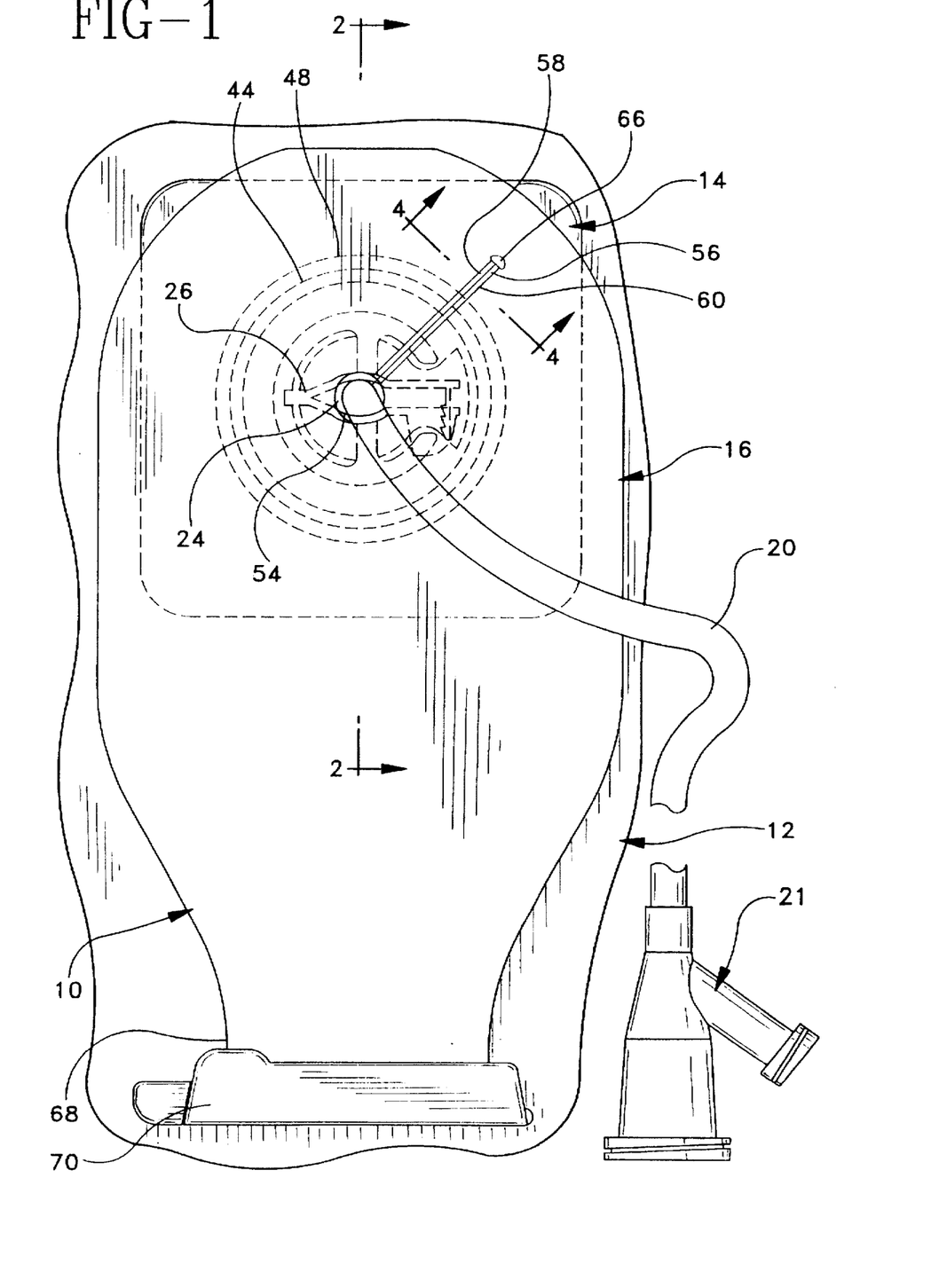
FIG. 1 is a plan view of a medical device in accordance with the present invention attached to the body of a patient.
Figure 2:
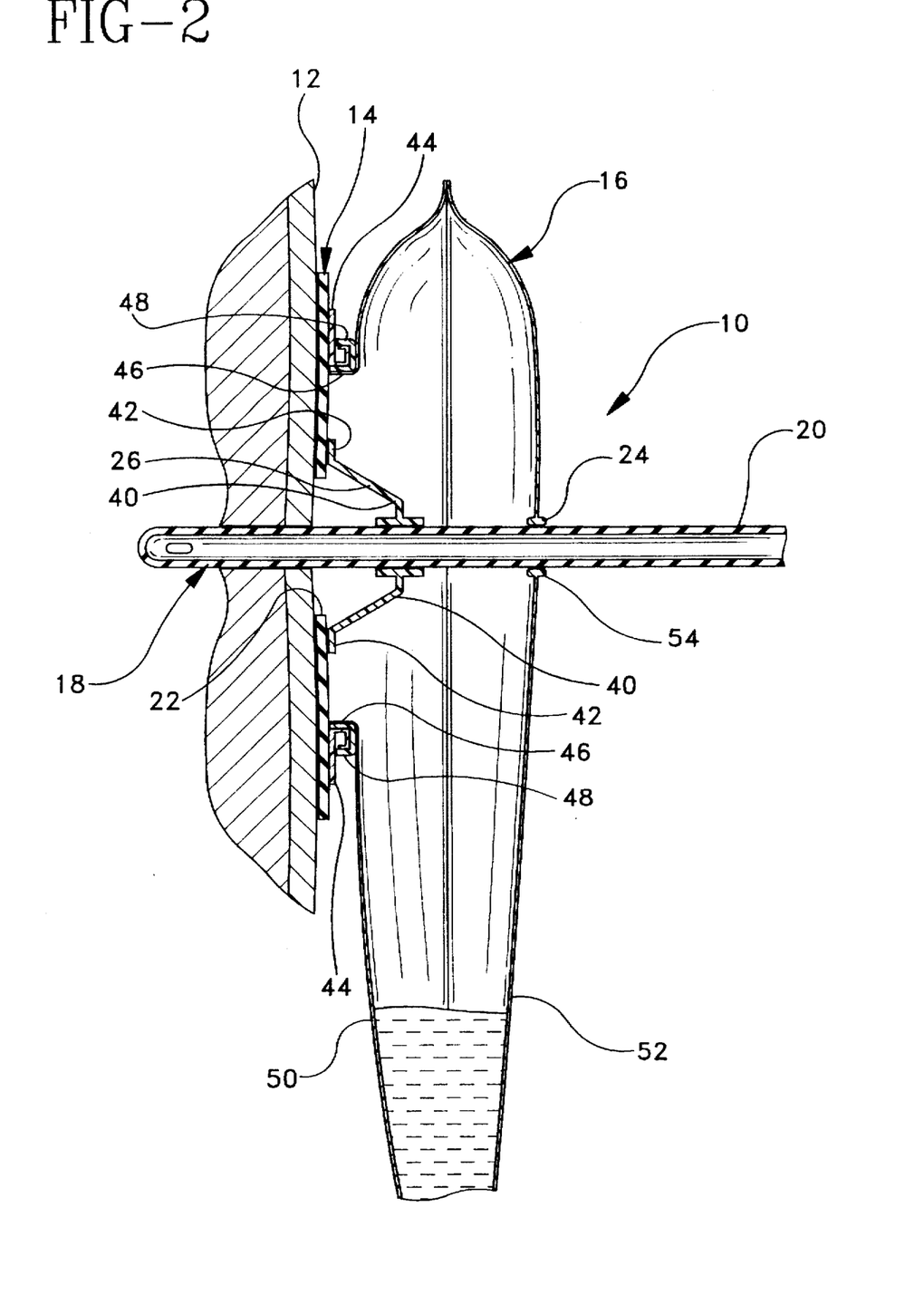
FIG. 2 is a partial sectional view of the device taken along line 2—2 of FIG. 1.

Referring to the drawings, FIG. 1 shows an assembled medical device 10 attached to skin tissue of a patient, such as abdominal wall 12. The device includes base plate 14 and drainage bag 16. As best seen in FIG. 2, base plate 14 is attached to the patient adjacent an opening such as stoma 18. The base plate may be fastened to the patient by any convenient method, such as a bio-compatible adhesive. The base plate may be made of any suitable material with a gauge (thickness) and modulus of elasticity such that it is able to transmit loads to the patient but conform to the surface of the patient's body. Plastic is a preferred material, but many other materials are possible. The base plate may have dimensions of, for example, 4 inches×4 inches×1/32 inch thick.

A catheter such as feeding tube 20 is introduced into stoma 18, or other skin-tissue opening, for the provision of a treating liquid, such as a medicament, an irrigating solution, or a feeding solution. An aperture 22 is formed in base plate 14 and is dimensioned to permit passage of a catheter such as feeding tube 20 therethrough. Feeding tube-engaging port 24, which can also be designed for use with other types of catheters, is formed in drainage bag 16 to permit passage of the tube or catheter through the bag.

Typical feeding tubes employed in gastrostomy are equipped with a bifurcated end 21 as shown in FIG. 1. In gastrostomy applications, such tubes are surgically placed in the patient and the base plate 14 must slide into place over the emplaced tube. Accordingly, for gastrostomy applications, aperture 22 is preferably configured and dimensioned to permit passage of bifurcated end 21. One possible configuration is the keyhole shape as shown in the drawings and best seen in FIG. 3. The bifurcated end 21 may be pinched together to facilitate passage through the aperture 22.

As another alternative to permit passage of bifurcated end 21, base plate 14 may be formed with a radial cut (not shown) emanating from aperture 22 to the perimeter of the base plate, or may even be formed in two pieces. Such a radial cut or two-piece construction will also aid in removing the base plate from the patient, but can increase the potential for leakage. It has been found that a fairly large aperture 22 is desirable in any case to permit application of medicaments to the skin tissue of the patient adjacent the stoma in order to combat irritation.

Figure 3:
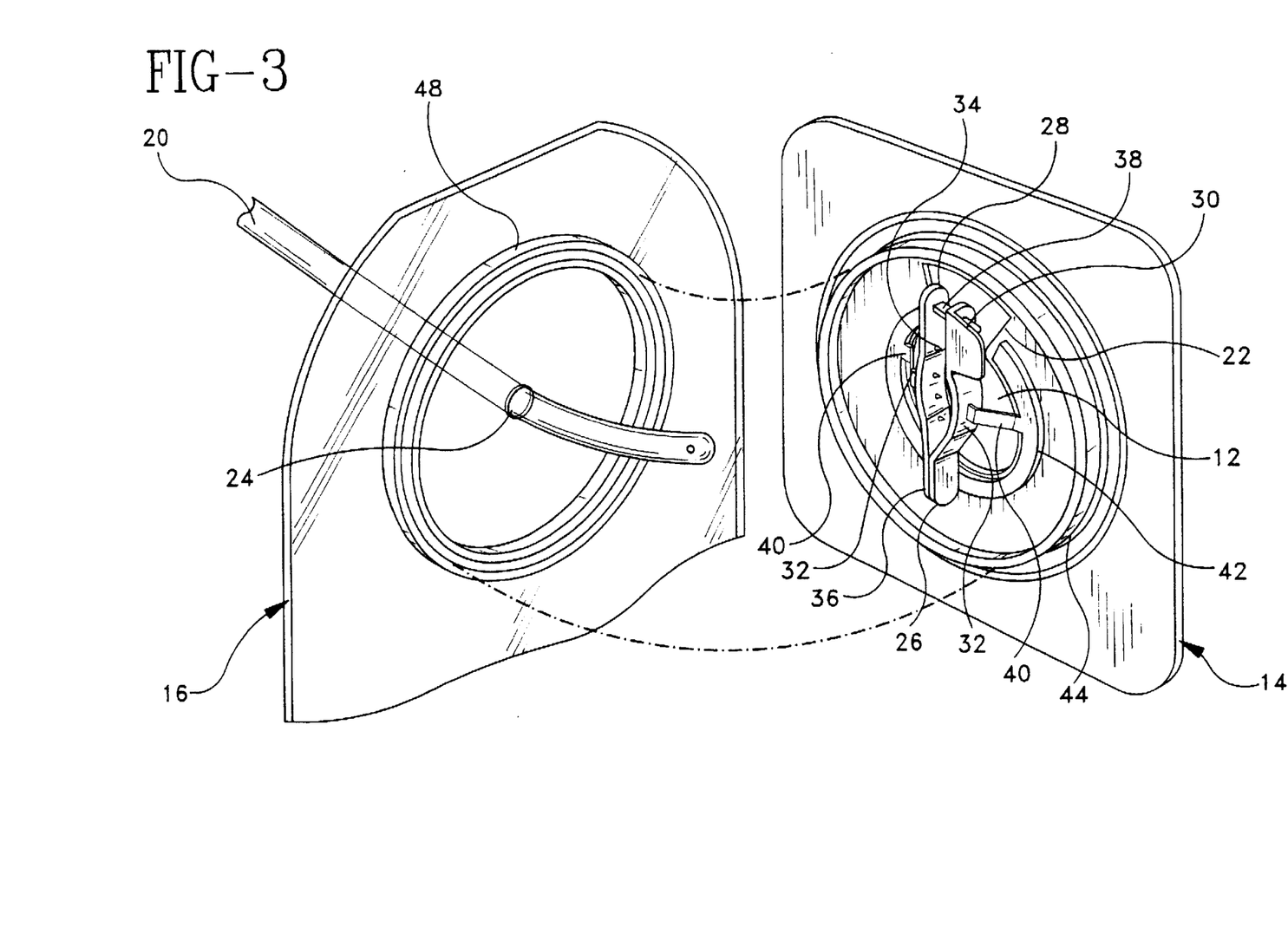
FIG. 3 is an exploded, enlarged detailed perspective view of the base plate of the device with an associated portion of the drainage bag.

As best seen in FIG. 3, a feeding tube retainer such as toothed clip assembly 26 mounted to base plate adjacent aperture 22 is provided for rigid fastening of tube 20. Rigid fastening, as used herein, is meant to encompass at least substantial fixity against compressive and tensile axial loads applied to the tube. Such loads are loads that would tend to force the tube further into the patient, or extract the tube from the patient, respectively. It has been found that providing fixity against both types of axial load substantially reduces or eliminates discomfort to the patient associated with shifting of the feeding tube.

The toothed clip assembly 26 preferably consists of substantially parallel clamping members 28, 30. Each member 28, 30 may be formed with a bulge 32 to accommodate tube 20. Blunt teeth 34 may be provided on the facing portions of the clamping members to engage the tube 20 for more secure clamping. Clamping members 28, 30 are preferably joined at fastening point 36. Relative motion may be provided by flexure of the clamping members, which may be locked in position by, for example, engagement of toothed ratchet 38 formed in member 28 with a mating ratchet-receiving orifice (not shown) in member 30.

Clamping members 28, 30 may be supported by projections 40 and by support 42 which is secured to base plate 14. Preferably, toothed clip assembly 26 is made of rigid plastic, but many other materials, such as light-gauge stainless steel, are also possible. Support 42 may be fastened to base plate 14 by any convenient means such as adhesive, ultrasonic welding, thermal bonding, or mechanical fastening, depending on the materials of construction. It will be understood that many other types of feeding tube or catheter retainers providing substantially rigid fastening are possible, and the aforementioned toothed clip is meant only to serve as an example.

Base plate 14 is also provided with a drainage bag retainer such as male snap ring 44. The male snap ring is disposed about aperture 22, and is configured and dimensioned to sealingly engage the drainage bag 16. Leakage of fluid from stoma 18 is thereby contained within bag 16. Referring again to FIGS. 1 and 2, drainage bag 16 is formed with base plate-engaging opening 46. The bag is designed to sealingly engage the drainage bag retainer of base plate 14 about a perimeter of opening 46. Preferably, this sealing engagement is provided by mating male snap ring 44 of base plate 14 with a sealing ring, such as female snap ring 48, formed in the perimeter of opening 46. The snap rings are preferably made of plastic, but can be manufactured of other materials; for example, they may be rolled from light gauge stainless steel.

Drainage bag 16 is preferably constructed of a flexible, biocompatible plastic material in sheet form. Preferably, two sheets of such material, such as first and second sides 50 and 52 respectively, are ultrasonically welded or thermally bonded about their perimeters to form the bag. Base plate-engaging opening 46 may be formed in first side 50, while feeding tube-engaging port 24 is preferably formed in second side 52.

Port 24 and opening 46 are arranged to permit simultaneous attachment of the bag to the base plate and cooperative passage of feeding tube 20, or other catheter, through the port 24, opening 46, and thus through bag 16. In a preferred embodiment of the bag, port 24 is disposed substantially opposite opening 46, which is located near the top of bag 16.

Cooperative passage as used herein refers to a relationship among the parts wherein the tube 20 may pass through the bag 16 without transmitting, in normal use, any excessive forces to the bag 16 that would cause it to rip or otherwise experience structural failure. As discussed below, cooperative passage is also intended to apply to passage of a tube through the bag via a bulkhead fitting employing multiple tube segments.

Feeding tube-engaging port 24 is preferably formed with a compliant circumferential seal 54. A typical diameter of the port/seal might be, for example, ⅝ inch. Seal 54 is preferably formed of a toroidal elastomeric member with sufficient compliance to sealingly engage catheters or feeding tubes of various diameters. Seal 54 may be fastened to second side 52 of bag 16 by a variety of methods, such as ultrasonic welding, thermal bonding, or adhesive bonding.

Preferably, port 24 and bag 16 are formed with a slit such as radial slit 56 extending through seal 54 into second side 52 of bag 16. Radial slit 56 may be dimensioned to facilitate the passage of tube 20 through port 24, and may have a radial length of, for example, 1 inch. Use of slit 56 is particularly advantageous in gastrostomy applications wherein bifurcated end 21 of tube 20 must be passed through bag 16. Slit 56 is shown for convenience at an angle of 45 degrees from the horizontal, however any convenient angular orientation can be used. A substantially vertical orientation is preferred to minimize leakage.

Figure 4:
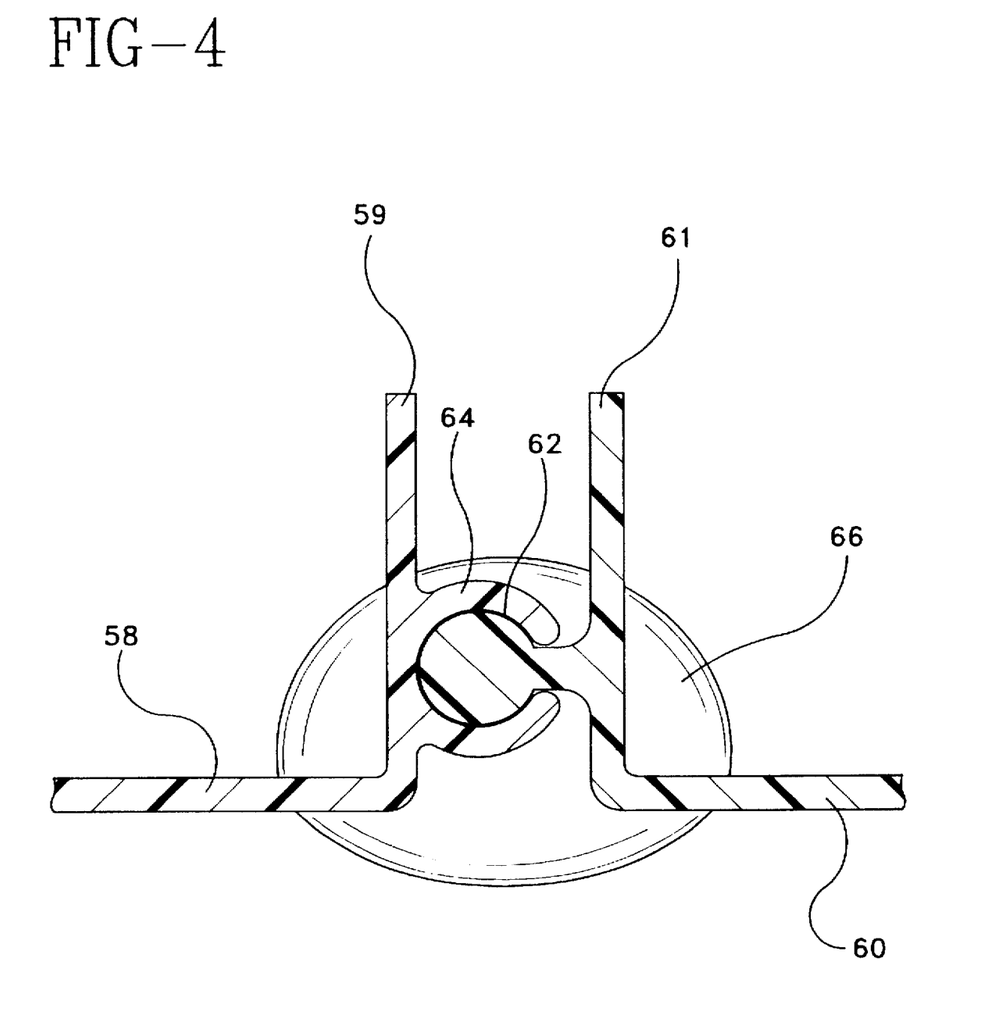
FIG. 4 is an enlarged sectional view of mating portions defining a radial slit of a drainage bag of the invention taken along line 4—4 in FIG. 1.

Slit 56 is formed with first and second edges 58 and 60 which are designed to sealingly mate after tube 20 is introduced into port 24. Preferably, edges 58 and 60 are provided with mating sealing members such as intermeshing convoluted ridge members 62 and 64, as best seen in FIG. 4. These members may be formed integrally with bag 16 or may be attached to it, and may be terminated, for example, in molded boss 66. Upstanding tabs 59 and 61 may be provided to facilitate mating and demating of members 62 and 64.

Preferably, seal 54 is dimensioned so that the faces (not shown) formed on each side of radial slit 56 have a sufficient interference fit with each other that they are placed in tangential compression upon mating of edges 58 and 60 of slit 56. The tangential compression will result in substantial sealing of the slit 56 in the region where it passes through the seal 54. Alternatively, seal 54 can also be provided with mating sealing members on its faces (not shown), which may, if desired, be continuations of members 62 and 64.

It is to be understood that many other approaches can be taken to providing a feeding tube-engaging port of a drainage bag arranged relative to a base plate-engaging opening of such a bag for cooperative passage of a tube through the bag. For example, many commercially available drainage bags are formed with a bottom opening 68 that may be sealed with a clip 70, as shown in FIG. 1. The clip 70 may be dispensed with and the bottom opening 68 may be used as the feeding tube-engaging port in lieu of item 24. Tube 20 may be passed from toothed clip assembly 26 down through the interior of bag 16 through bottom opening 68. A ligature such as an ordinary rubber band may then be used to gather and seal the portions of bag 16 adjacent bottom opening 68 about tube 20.

Figure 5:
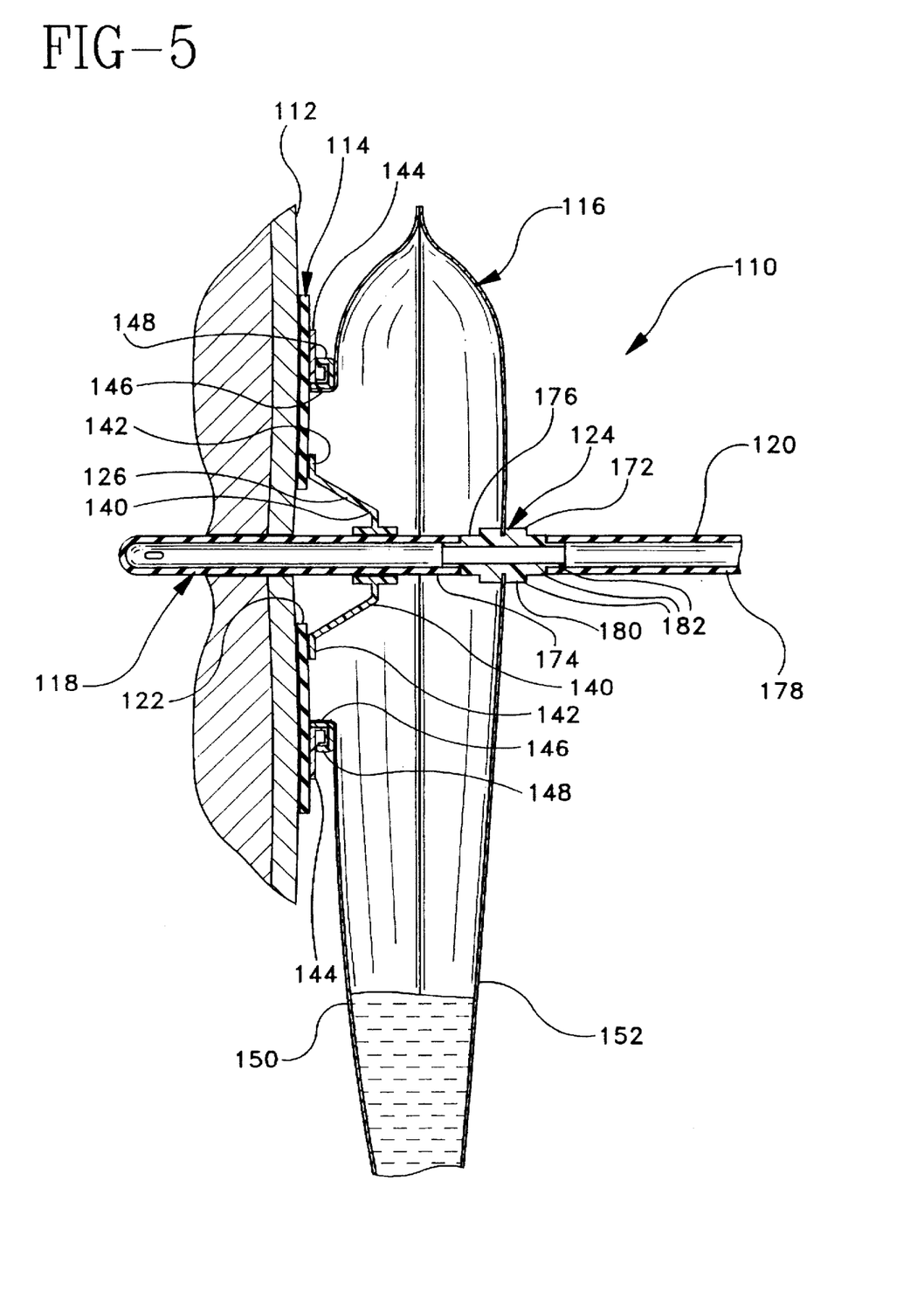
FIG. 5 is a view similar to FIG. 2 showing an alternative embodiment of the invention.

An alternative embodiment of the invention is shown in FIG. 5, wherein elements similar to those in the embodiment of FIG. 2 are given the same reference characters incremented by 100. Port 124 is formed as a bulkhead fitting 172 having an internal bore and designed to receive feeding tube segments on either side of second side 152 of bag 116. An inner sediment 174 of the feeding tube 120 having a predetermined length is attached to an inner side 176 of the fitting, while an outer segment 178 of tube 120 is attached to an outer side 180 of fitting 172. Fitting 172 may be provided with steps 182 having different outside diameters corresponding to different inside diameters of feeding tubes or other catheters to be employed with the invention. The bulkhead fitting is preferably made of plastic ultrasonically welded to the bag but can also be fastened to the bag by mechanical or other suitable means. As used in the specification and the appended claims, cooperative passage of a feeding tube through a drainage bag is intended to encompass use of a tube having multiple tube segments that are attached to a bulkhead fitting.

In a method according to the invention for simultaneous feeding and venting of bodily fluids through a stoma (or other opening) of a patient, a medical device according to the invention is attached to a patient. In the case of the embodiment of FIG. 2, such attachment may, for example, be performed as follows. The feeding tube 20, or other catheter to be employed, is inserted into the patient. Frequently, for example in gastrostomy, such insertion is done at the time of surgery, after which the tube remains in the patient. The skin tissue of the patient adjacent the opening, such as abdominal wall 12 adjacent stoma 18, is cleaned.

Feeding tube 20 or other catheter to be employed is passed through aperture 22 of base plate 14, and base plate 14 is then secured to the patient. Appropriate powdered preparations may be applied to the abdominal wall to aid in adhesion of the base plate. The tube is subsequently clamped in place by a feeding tube retainer such as toothed clip assembly 26 that provides substantially rigid fastening.

Bifurcated end 21 of tube 20 is then passed through base plate-engaging opening 46 and radial slit 56 of drainage bag 16. The bag 16 is slidably moved along the tube 20 until the female snap ring 48 engages male snap ring 44, thereby fastening and sealing bag 16 to base plate 14. Finally, mating ridge members 62 and 64 are sealingly engaged with each other as tube 20 is moved radially into feeding tube-engaging port 24. It will be understood that alternative methods of assembly are possible.

The embodiment of FIG. 5 may be attached to the patient, for example, according to the following procedure. Inner segment 174 of tube 120 is inserted into the patient as above, and the base plate 114 is attached as above. Inner segment 174 is then clamped in place by toothed clip assembly 126, and fastened to inner side 176 of bulkhead fitting 172. Outer segment 178 of tube 120 is then fastened to outer side 180 of bulkhead fitting 172. Finally, female snap ring 148 of bag 116 is mated with male snap ring 144 of base plate 114.

In operation, a fluid such as a feeding solution or a medicament is supplied to tube 20 and caused to flow into the alimentary tract of a patient through stoma 18. The flow may be driven by hydrostatic pressure in an IV-type bag or other fluid reservoir, or may be produced with a hand or mechanically operated pump, such as a peristaltic pump. Any liquid draining from the stoma around the outside of the tube 20, whether back flow of the supplied fluid, or other fluid such as gastric juices, is captured in the drainage bag.

The toothed clip assembly 26 of other feeding tube retainer prevents motion of the feeding tube 20 within the patient, whether from patient motion, hydrodynamic reactive forces on the tube, or other source. Once the drainage bag 16 is filled to a predetermined level, or after it has been in place a predetermined time, the patient can be maneuvered into a position such that fluid is drained to a portion of the bag away from any leakage paths, and the bag can be removed and disposed of. If desired, the bag may be drained and reused. It has also been found that replacement of the base plate, which may be necessary as frequently as every 4–5 days due to degradation of the adhesive, can be accomplished with minimal discomfort to the patient if the patient holds the tube while the nurse or other practitioner removes the base plate.

It will be understood that usage is similar when the device is employed in other modes of operation such as wound irrigation and drainage, wherein a catheter is introduced through an opening in skin tissue of a patient such as a wound.

While there have been described what are presently believed to be the preferred embodiments of the invention, those skilled in the art will realize that various changes and modifications may be made to the invention without departing from the spirit of the invention, and it is intended to claim all such changes and modifications as fall within the scope of the invention.

What is claimed is:

1. A medical device for holding a feeding tube, comprising:
    a base plate for attachment to an abdominal wall of a patient adjacent a stoma of said patient, said base plate having an aperture therethrough, said aperture being dimensioned to permit passage of a feeding tube;
    a feeding tube retainer secured to said base plate adjacent said aperture, said feeding tube retainer providing substantially rigid fastening of the feeding tube to said base plate;
    a drainage bag retainer located on said base plate, said drainage bag retainer being disposed about said aperture, said drainage bag retainer being configured and dimensioned to sealingly engage a drainage bag about a perimeter of a base plate-engaging opening; and
    a drainage bag, said bag having a base plate-engaging opening and a feeding tube-engaging port arranged relative to said opening to permit simultaneous attachment of said bag to said plate and cooperative passage of said feeding tube therethrough said feeding tube retainer being located within said drainage bag.

2. The medical device of claim 1, wherein:

said drainage bag has at least first and second sides;

said base plate-engaging opening is formed in said first side of said drainage bag; and said feeding tube-engaging port is formed in said second side of said drainage bag substantially opposite said base plate-engaging opening in said first side of said drainage bag.

3. The medical device of claim 1, wherein said perimeter of said base plate-engaging opening is formed with a sealing ring, said sealing ring providing substantially leak-tight mechanical engagement with said drainage bag retainer.

4. The medical device of claim 1, wherein said feeding tube-engaging port is formed with a compliant circumferential seal to sealingly engage feeding tubes of various diameters.

5. The medical device of claim 4, wherein said drainage bag and said feeding tube-engaging port are formed with a radial slit emanating from said port and extending into said bag, said slit being dimensioned to facilitate passage of the feeding tube through said port, said slit having first and second edges, said edges being equipped with mating sealing members.

6. The medical device of claim 5, wherein said mating sealing members are intermeshing convoluted ridge members.

7. The medical device of claim 1, wherein said feeding tube-engaging port is a bulkhead fitting adapted to receive first and second segments of the feeding tube.

8. The medical device of claim 7, wherein said bulkhead fitting is stepped to engage feeding tubes having various diameters.

9. A medical device for holding a catheter, comprising:

a base plate for attachment to skin tissue of a patient adjacent an opening in said skin tissue of said patient, said base plate having an aperture therethrough, said aperture being dimensioned to permit passage of a catheter;

a catheter retainer secured to said base plate adjacent said aperture, said catheter retainer providing substantially rigid fastening of the catheter to said base plate;

a drainage bag retainer located on said base plate, said drainage bag retainer being disposed about said aperture, said drainage bag retainer being configured and dimensioned to sealingly engage a drainage bag about a perimeter of a base plate-engaging opening; and a drainage bag, said bag having a base plate-engaging opening and a catheter-engaging port arranged relative to said opening to permit simultaneous attachment of said bag to said plate and cooperative passage of said catheter therethrough, said catheter retainer being located within said drainage bag.

10. A method for simultaneous feeding and venting of bodily fluids through a stoma, comprising attaching to a patient a medical device for holding a feeding tube, said device having:

a base plate for attachment to an abdominal wall of a patient adjacent a stoma of said patient, said base plate having an aperture therethrough, said aperture being dimensioned to permit passage of a feeding tube;

a feeding tube retainer secured to said base plate adjacent said aperture, said feeding tube retainer providing substantially rigid fastening of the feeding tube to said base plate;

a drainage bag retainer located on said base plate, said drainage bag retainer being disposed about said aperture, said drainage bag retainer being configured and dimensioned to sealingly engage a drainage bag about a perimeter of a base plate-engaging opening; and a drainage bag, said bag having a base plate-engaging opening and a feeding tube-engaging port arranged relative to said opening to permit simultaneous attachment of said bag to said plate and cooperative passage of said feeding tube therethrough, said feeding tube retainer being located within said drainage bag.

11. A medical device for holding a feeding tube, comprising:

a base plate for attachment to an abdominal wall of a patient adjacent a stoma of said patient, said base plate having an aperture therethrough, said aperture being dimensioned to permit passage of a feeding tube;

a feeding tube retainer secured to said base plate adjacent said aperture, said feeding tube retainer providing substantially rigid fastening of the feeding tube to said base plate, said feeding tube retainer having at least first and second positions, said feeding tube retainer permitting substantially free axial passage of the tube in said first position, said feeding tube retainer providing said substantially rigid fastening in said second position;

a drainage bag retainer located on said base plate, said drainage bag retainer being disposed about said aperture, said drainage bag retainer being configured and dimensioned to sealingly engage a drainage bag about a perimeter of a base plate-engaging opening; and a drainage bag, said bag having a base plate-engaging opening and a feeding tube-engaging port arranged relative to said opening to permit simultaneous attachment of said bag to said plate and cooperative passage of said feeding tube therethrough.

12. The medical device of claim 11, wherein:

said drainage bag has at least first and second sides;

said base plate-engaging opening is formed in said first side of said drainage bag; and said feeding tube-engaging port is formed in said second side of said drainage bag substantially opposite said base plate-engaging opening in said first side of said drainage bag.

13. The medical device of claim 11, wherein said perimeter of said base plate-engaging opening is formed with a sealing ring, said sealing ring providing substantially leak-tight mechanical engagement with said drainage bag retainer.

14. The medical device of claim 11, wherein said feeding tube-engaging port is formed with a complaint circumferential seal to sealingly engage feeding tubes of various diameters.

15. The medical device of claim 14, wherein said drainage bag and said feeding tube-engaging port are formed with a radial slit emanating from said port and extending into said bag, said slit being dimensioned to facilitate passage of the feeding tube through said port, said slit having first and second edges, said edges being equipped with mating sealing members.

16. The medical device of claim 15, wherein said mating sealing members are intermeshing convoluted ridge members.

17. The medical device of claim 11, wherein said feeding tube-engaging port is a bulkhead fitting adapted to receive first and second segments of the feeding tube.

18. The medical device of claim 17, wherein said bulkhead fitting is stepped to engage feeding tubes having various diameters.

19. A medical device for holding a catheter, comprising:

a base plate for attachment to skin tissue of a patient adjacent an opening in said skin tissue of said patient, said base plate having an aperture therethrough, said aperture being dimensioned to permit passage of a catheter;

a catheter retainer secured to said base plate adjacent said aperture, said catheter retainer providing substantially rigid fastening of the catheter to said base plate, said catheter retainer having at least first and second positions, said catheter retainer permitting substantially free axial passage of the catheter in said first position, said catheter retainer providing said substantially rigid fastening in said second position;

a drainage bag retainer located on said base plate, said drainage bag retainer being disposed about said aperture, said drainage bag retainer being configured and dimensioned to sealingly engage a drainage bag about a perimeter of a base plate-engaging opening; and a drainage bag, said bag having a base plate-engaging opening and a catheter-engaging port arranged relative to said opening to permit simultaneous attachment of said bag to said plate and cooperative passage of said catheter therethrough.

20. A method for simultaneous feeding and venting of bodily fluids through a stoma, comprising attaching to a patient a medical device for holding a feeding tube, said device having:

a base plate for attachment to an abdominal wall of a patient adjacent a stoma of said patient, said base plate having an aperture therethrough, said aperture being dimensioned to permit passage or a feeding tube;

a feeding tube retainer secured to said base plate adjacent said aperture, said feeding tube retainer providing substantially rigid fastening of the feeding tube to said base plate, said feeding tube retainer having at least first and second positions, said feeding tube retainer permitting substantially free axial passage of the tube in said first position, said feeding tube retainer providing said substantially rigid fastening in said second position;

a drainage bag retainer located on said base plate, said drainage bag retainer being disposed about said aperture, said drainage bag retainer being configured and dimensioned to sealingly engage a drainage bag about a perimeter of a base plate-engaging opening; and a drainage bag, said bag having a base plate-engaging opening and a feeding tube-engaging port arranged relative to said opening to permit simultaneous attachment of said bag to said plate and cooperative passage of said feeding tube therethrough.

* * * * *

UNITED STATES PATENT AND TRADEMARK OFFICE
CERTIFICATE OF CORRECTION

PATENT NO. : 5,738,661
DATED : April 14, 1998
INVENTOR(S) : Gennaro Larice

It is certified that error appears in the above-identified patent and that said Letters Patent is hereby corrected as shown below:

<u>In Column 3, Line 31,</u>  the patent now reads --mounted to base plate adjacent--; this should read --mounted to base plate 14 adjacent--.

<u>In Column 5, Line 25,</u>  the patent now reads --inner sediment 174--; this should read --inner segment 174--.

Signed and Sealed this

Sixteenth Day of June, 1998

*Attest:*

BRUCE LEHMAN

*Attesting Officer*   *Commissioner of Patents and Trademarks*